(12) United States Patent
McKiernan et al.

(10) Patent No.: US 8,409,664 B2
(45) Date of Patent: Apr. 2, 2013

(54) SUPERABSORBENT POLYMER PARTICLES COATED WITH A HYDROPHILIC ELASTOMER AND ABSORBENT ARTICLE COMPRISING SUCH PARTICLES

(75) Inventors: Robin Lynn McKiernan, Mason, OH (US); Steve Daryl Smith, Fairfield, OH (US); Axel Meyer, Frankfurt (DE)

(73) Assignee: The Procter & Gamble Company, Cincinnati, OH (US)

( * ) Notice: Subject to any disclaimer, the term of this patent is extended or adjusted under 35 U.S.C. 154(b) by 140 days.

(21) Appl. No.: 13/169,107

(22) Filed: Jun. 27, 2011

(65) Prior Publication Data

US 2011/0319847 A1 Dec. 29, 2011

Related U.S. Application Data

(60) Provisional application No. 61/359,123, filed on Jun. 28, 2010.

(51) Int. Cl.
*C08L 53/00* (2006.01)
*A61L 15/60* (2006.01)
*A61L 15/22* (2006.01)

(52) U.S. Cl. ......... 427/212; 428/402; 428/407; 604/368

(58) Field of Classification Search ............... 427/212; 428/402, 407; 604/368; 525/93, 94
See application file for complete search history.

(56) References Cited

U.S. PATENT DOCUMENTS

| 3,567,798 A | 3/1971 | Haefele et al. |
| 2008/0200331 A1 | 8/2008 | Daniel et al. |
| 2010/0228213 A1 | 9/2010 | Berland et al. |

FOREIGN PATENT DOCUMENTS

| EP | 0566896 | 10/1993 |
| EP | 0887368 | 12/1998 |
| WO | WO 2005/014065 A1 | 2/2005 |

OTHER PUBLICATIONS

International Search Report, PCT/US2011/042117, dated Sep. 6, 2011, 10 pages.
International Search Report, PCT/US2011/042116, mailed Oct. 7, 2011, 10 pages.

*Primary Examiner* — Jeffrey Mullis
(74) *Attorney, Agent, or Firm* — Andrew A Paul

(57) ABSTRACT

Superabsorbent polymer particles, coated with a block copolymer comprising at least four blocks being at least two hard blocks, one soft block and one hydrophilic block, wherein a the soft block is sandwiched between the hard blocks.

21 Claims, 1 Drawing Sheet

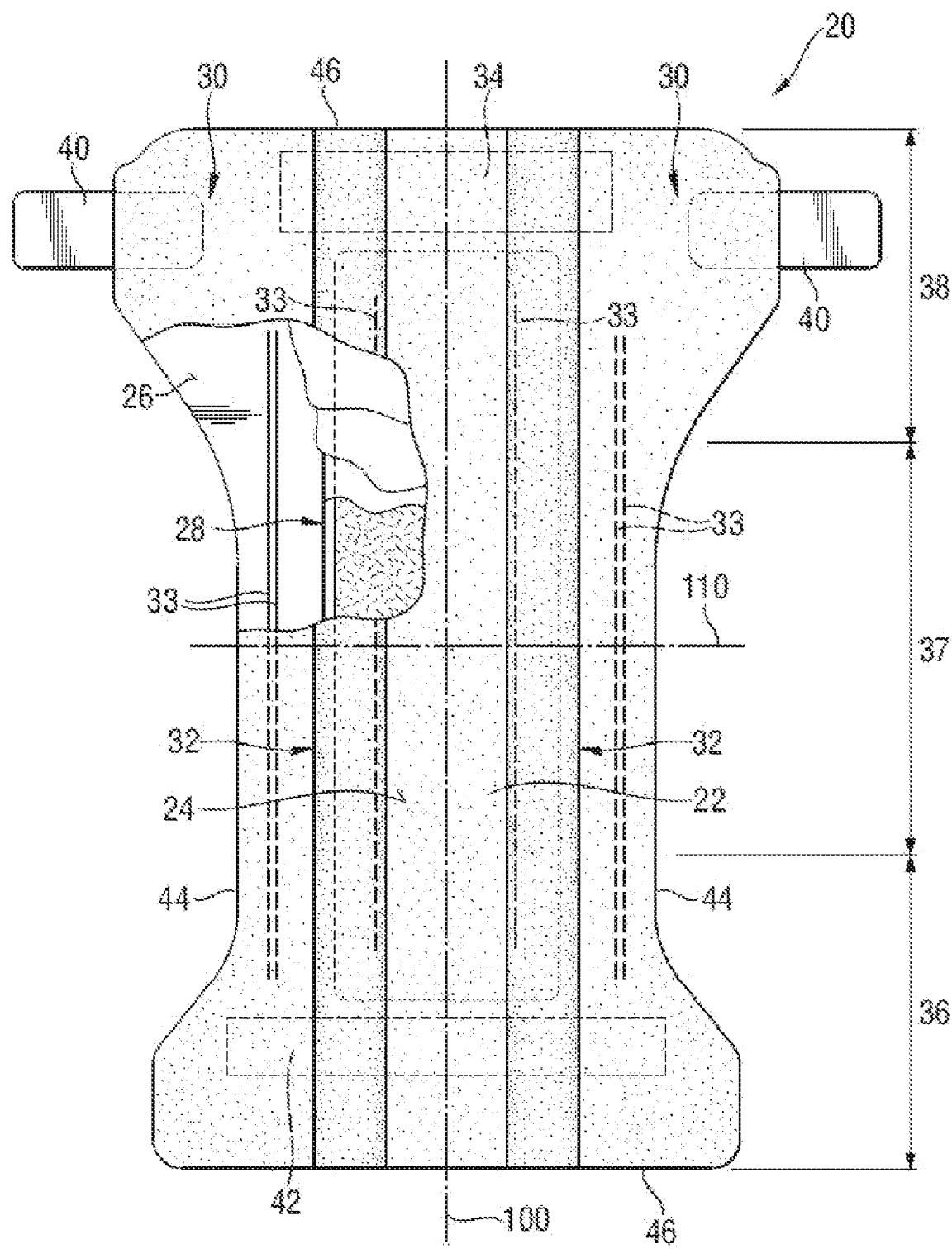

SUPERABSORBENT POLYMER PARTICLES COATED WITH A HYDROPHILIC ELASTOMER AND ABSORBENT ARTICLE COMPRISING SUCH PARTICLES

CROSS REFERENCE TO RELATED APPLICATION

This application claims the benefit of U.S. Provisional Application No. 61/359,123, filed on Jun. 28, 2010.

FIELD OF THE INVENTION

The invention relates to superabsorbent material, such as superabsorbent polymer particles, comprising a hydrophilic elastomeric water vapor permeable coating. The coating is intended to allow swelling of the coated superabsorbent polymer particles without breakage of the coating, and, at the same time ensure good transport of water based liquids through the coating into the superabsorbent polymer particle.

The invention also relates to diapers, adult incontinence articles and catamenial devices, such as sanitary napkins, comprising said coated water swellable material.

The invention further relates to a process of making such a superabsorbent material comprising the hydrophilic elastomeric water vapor permeable coating.

BACKGROUND OF THE INVENTION

An important component of disposable absorbent articles such as diapers is an absorbent core structure comprising superabsorbent polymers, typically hydrogel-forming superabsorbent polymers, also referred to as absorbent gelling material (AGM), or super-absorbent polymers. This polymer material ensures that large amounts of bodily fluids, e.g. urine, can be absorbed by the article during its use and locked away, thus providing low rewet and good skin dryness.

Superabsorbent polymers are often made by initially polymerizing unsaturated carboxylic acids or derivatives thereof, such as acrylic acid, alkali metal (e.g., sodium and/or potassium) or ammonium salts of acrylic acid, alkyl acrylates, and the like in the presence of relatively small amounts of di- or poly-functional monomers such as N,N'-methylene-bis-acrylamide, trimethylolpropane triacrylate, ethylene glycol di(meth)acrylate, or triallylamine. The di- or poly-functional monomer materials serve to lightly cross-link the polymer chains thereby rendering them water-insoluble, yet water-swellable. These lightly crosslinked superabsorbent polymers contain a multiplicity of neutralized carboxylate groups attached to the polymer backbone. It is generally believed, that these carboxylate groups generate an osmotic driving force for the absorption of body fluids by the crosslinked polymer network.

Typically, the superabsorbent polymers are provided in particulate form.

In addition, the superabsorbent polymer particles are often treated as to form a surface cross-linked layer on the outer surface in order to improve their properties in particular for application in baby diapers.

Generally, superabsorbent polymers useful as absorbents in absorbent members and articles such as disposable diapers need to have adequately high sorption capacity, as well as adequately high gel strength. Sorption capacity needs to be sufficiently high to enable the absorbent polymer to absorb significant amounts of the aqueous body fluids encountered during use of the absorbent article. Together with other properties of the gel, gel strength relates to the tendency of the swollen superabsorbent polymer particles to resist deformation under an applied stress in the absorbent article. The gel strength needs to be high enough in the absorbent article so that the superabsorbent polymer particles do not deform and fill the capillary void spaces to an unacceptable degree causing so-called gel blocking. This gel-blocking inhibits the rate of fluid uptake or the fluid distribution, i.e. once gel-blocking occurs, it can substantially impede the distribution of fluids to relatively dry zones or regions in the absorbent article and leakage from the absorbent article can take place well before the superabsorbent polymer particles are fully saturated or before the fluid can diffuse or wick past the "blocking" particles into the rest of the absorbent article. Thus, it is important that the superabsorbent polymer particles (when incorporated in an absorbent structure or article) maintain a high wet-porosity and have a high resistance against deformation thus yielding high permeability for fluid transport through the swollen gel bed.

Superabsorbent polymers with relatively high permeability can be made by increasing the level of internal crosslinking or surface crosslinking, which increases the resistance of the swollen gel against deformation by an external pressure such as the pressure caused by the wearer, but this typically also reduces the absorbent capacity of the gel undesirably.

Often the surface crosslinked superabsorbent polymer particles are constrained by the surface-crosslinking 'shell' and cannot absorb and swell sufficiently, and/or that the shell is not strong enough to withstand the stresses of swelling or the stresses associated with performance under load.

It has been proposed in recent years to coat superabsorbent polymer particles with elastomeric film forming polymers, for example in WO2005/014065.

The inventors have developed new superabsorbent polymer particles coated with a specific block copolymer as described herein. The resulting coated superabsorbent polymer particles have been found to show a good transportation of water based liquids through the coating into the superabsorbent polymer particles, a good stability of the coating upon expansion of the superabsorbent polymers and a good liquid transport between the coated superabsorbent particles. These properties in combination improve liquid transport and absorption properties of the coated superabsorbent particles described herein.

SUMMARY OF THE INVENTION

Coated superabsorbent polymer particles, being coated with a block copolymer, wherein the block copolymer is obtainable by preparing a sequence of soft block(s) (A) and hard blocks (B), the sequence comprising at least three blocks being at least a first soft block, a first hard block and a second hard block wherein the first soft block is sandwiched between the first and second hard blocks (B), combining the sequence of soft block(s) and hard blocks with a hydrophilic block (C) block, or combining the sequence of soft block(s) and hard blocks with a hydrophilic block precursor and subsequently transforming the hydrophilic block precursor into the hydrophilic block (C).

Without wishing to be bound by theory, it is believed that due to the specific selection of the four or more blocks of the block copolymer a coating providing good liquid transport into the superabsorbent particles, paired with good stability of the coating which can help to accommodate expansion of the superabsorbent particle can be achieved.

It is, for example, believed that the good liquid transport through the coating is positively influenced by the high water vapor transmission rate of the block copolymers, and that the good stability of the coating results from its elastic extensibility.

BRIEF DESCRIPTION OF THE DRAWINGS

FIG. 1 shows a diaper as an exemplary embodiment of an absorbent article.

DETAILED DESCRIPTION OF THE INVENTION

Definition of Terms

"Block copolymer" refers to copolymers comprising different polymeric subunits (blocks) wherein the individual blocks are covalently bound to each other.

The individual "blocks" are typically composed of monomeric units. The term "monomeric unit", instead of monomer, is used in order to refer to a sequence of polymerized monomers having the same chemical composition irrespective of their synthesis. For example, polystyrene is a polymer obtained by the polymerization of the monomer styrene. Polystyrenesulfonate on the other hand may be obtained by polymerization of styrenesulfonate monomers or by sulfonation of polystyrene. Irrespective of the chosen synthesis, it comprises monomeric units of styrene sulfonate. Herein the "block length" (i.e. the length of an individual block) is expressed by the number of same or similar monomeric units which are directly covalently bound to each other. Generally, a block comprises at least 10 monomeric units.

The "hydrophilic block" herein refers to a block which is added to the sequence of soft block(s) and hard blocks in order to enhance the affinity of the resulting block copolymer towards water. Typically, the hydrophilic block is comprised of, or consists of, hydrophilic monomeric units. Generally, monomeric units that enhance the affinity of the resultant polymer towards water will be considered hydrophilic. Typical hydrophilic monomeric units comprise functional groups such as polar and/or charged functional groups, for example hydrophilic monomeric units comprise one or more functional groups selected from the group consisting of acid groups in their free acid and salt form, ether groups, amine functionalized groups, quaternary ammonium groups, alcoholic groups and combinations thereof. Typically, the hydrophilic block increases the hydrophilicity of the block copolymer. For example, the block copolymer may have a smaller contact angle than the sequence of soft block(s) and hard blocks.

"Soft block" as used herein refers to a polymeric block having a glass transition temperature of below 20° C., or below 10° C., for example below 0° C.

"Hard block" as used herein refers to a polymeric block having a glass transition temperature of at least 40° C., or at least 80, for example at least 100° C.

"Elastomeric" when used herein means that the material will exhibit stress induced deformation that is partially or completely reversed upon removal of the stress.

"Absorbent article" herein refers to an article generally capable of absorbing and storing exudates discharged from the body. Absorbent articles are typically placed against or in proximity to the body of a wearer to absorb and contain the exudates discharged from the body, such as urine, blood or menses.

Typical absorbent articles may be diapers, such as pant-like diapers or taped diapers, sanitary napkins, panty liners, adult incontinence briefs, adult incontinence undergarments, absorbent inserts, tampons and the like.

"Diaper" refers to an absorbent article that is intended to be worn by wearer about the lower torso to absorb and contain exudates discharged from the body.

Diapers are typically worn by infants (e.g. babies or toddlers) and may be taped diapers which are provided with unfastened fastening elements or as in pant-like diapers having fixed sides in order to from a waist and leg openings. The fixed sides may be permanently or refastenably fixed to each other. Generally, pant-like diapers are placed in position on the wearer by inserting the wearer's legs into the leg openings and sliding the pant-like diaper into position about the wearer's lower torso.

"Disposable" refers to items that are intended to be discarded after a limited number of uses, frequently a single use (i.e., the original absorbent article as a whole is not intended to be laundered or reused as an absorbent article, although certain materials or portions of the absorbent article may be recycled, reused, or composted). For example, certain disposable absorbent articles may be temporarily restored to substantially full functionality through the use of removable/replaceable components but the article is nevertheless considered to be disposable because the entire article is intended to be discarded after a limited number of uses. Typically, the absorbent articles referred to herein are disposable, for example disposable diapers.

"Absorbent core" refers to a member of an absorbent article that is intended to absorb and store exudates discharged from the body. The absorbent core typically comprises absorbent material and, optionally, a core wrap. Optionally, the absorbent core may comprise a glue, such as a micro-fiber glue.

Superabsorbent Polymer Particles

The superabsorbent polymers herein are typically in the form of particles (which includes, for example, particles in the form of flakes, fibers, agglomerates). The superabsorbent polymer particles may be spherical in shape as well as irregularly shaped.

Useful herein are in principle all superabsorbent polymers known to one skilled in the art from superabsorbent literature, for example, as described in Modern Superabsorbent Polymer Technology, F. L. Buchholz, A. T. Graham, Wiley 1998. For example, the superabsorbent polymer particles are spherical particles which may be as obtained from inverse phase suspension polymerizations; optionally, the superabsorbent polymer particles may be agglomerated at least to some extent to form larger.

Olefinically unsaturated carboxylic acid and anhydride monomers useful herein include the acrylic acids typified by acrylic acid itself, methacrylic acid, α-chloroacrylic acid, α-cyanoacrylic acid, β-methylacrylic acid (crotonic acid), α-phenylacrylic acid, β-acryloxypropionic acid, sorbic acid, α-chlorosorbic acid, angelic acid, cinnamic acid, p-chlorocinnamic acid, β-stearylacrylic acid, itaconic acid, citroconic acid, mesaconic acid, glutaconic acid, aconitic acid, maleic acid, fumaric acid, tricarboxyethylene, and maleic anhydride.

In some embodiments, superabsorbent polymers of the superabsorbent polymer particles contain carboxyl groups, such as the above-described carboxylic acid/carboxylate containing groups. These superabsorbent polymers include hydrolyzed starch-acrylonitrile graft copolymers, partially neutralized hydrolyzed starch-acrylonitrile graft copolymers, starch-acrylic acid graft copolymers, partially neutralized starch-acrylic acid graft copolymers, hydrolyzed vinyl acetate-acrylic ester copolymers, hydrolyzed acrylonitrile or acrylamide copolymers, slightly network crosslinked polymers of any of the aforementioned copolymers, polyacrylic acid, and slightly network crosslinked polymers of polyacrylic acid.

The superabsorbent polymers for the superabsorbent polymer particles may be obtainable by polymerization of a monomer solution comprising:
  i) at least one ethylenically unsaturated acid-functional monomer,
  ii) at least one crosslinker,
  iii) if appropriate one or more ethylenically and/or allylically unsaturated monomers copolymerizable with i) and
  iv) if appropriate one or more water-soluble polymers onto which the monomers i), ii) and if appropriate iii) can be at least partially grafted,
  wherein the superabsorbent polymer obtained thereby may be dried, classified and if appropriate may be subsequently treated with
  v) at least one post-crosslinker (or: surface cross-linker)
before being dried and optionally post-crosslinked (i.e., surface crosslinked).

Useful monomers i) include, but are not limited to, ethylenically unsaturated carboxylic acids, such as acrylic acid, methacrylic acid, maleic acid, fumaric acid, and itaconic acid, or derivatives thereof, such as acrylamide, methacrylamide, acrylic esters and methacrylic esters. In some typical embodiments the monomers are either acrylic acid or methacrylic acid.

In typical embodiments, the superabsorbent polymers may be crosslinked, in such embodiments the polymerization may be carried out in the presence of compounds having two or more polymerizable groups which can be free-radically copolymerized into the polymer network.

The preparation of a suitable superabsorbent polymers and further examples of useful ethylenically unsaturated monomers i) are for example described in DE-A 199 41 423, EP-A 686 650, WO 01/45758 and WO 03/14300.

The acid groups of the superabsorbent polymers may be neutralized by 30-100 mol %, or 65-90 mol %, for example 72-85 mol % neutralized, for which the customary neutralizing agents can be used.

Neutralization may be carried out after polymerization. In some embodiments, up to 40 mol %, such as from 10 to 30 mol % or for example from 15 to 25 mol % of the acid groups may be neutralized before polymerization by adding a portion of the neutralizing agent to the monomer solution. In such embodiments, a further neutralization step may still be conducted after polymerization.

In typical embodiments, the superabsorbent polymers comprise from about 50% to 95% (mol percentage), for example about 75 mol % neutralized, crosslinked, polyacrylic acid (i.e., poly (sodium acrylate/acrylic acid)).

The neutralized polymer may then be dried for example with a belt, fluidized bed, tower dryer or drum dryer until the residual moisture content may be below 13% by weight, such as below 8% by weight, for example below 4% by weight, the water content being determined according to EDANA's recommended test method No. 430.2-02 "Moisture content" (EDANA=European Disposables and Nonwovens Association). The dried polymer may be ground and sieved thereafter. Exemplary grinding apparatuses typically include roll mills, pin mills, hammer mills, jet mills or swing mills.

The superabsorbent polymers may optionally be post-crosslinked (surface crosslinked) before the block copolymer (coating composition) is applied.

Typical post-crosslinkers include compounds comprising two or more groups capable of forming covalent bonds with the carboxylate groups of the polymers. The post-crosslinker may typically be used in an amount of about 1.50 wt. % or less, but typically not more than 0.50% by weight, or not more than 0.30% by weight, for example in the range from 0.001% and 0.15% by weight, all percentages being based on the superabsorbent polymer. It is possible to use a single post-crosslinker from the above selection or any desired mixtures of various post-crosslinkers.

The concentration of the at least one post-crosslinker v) in the aqueous post-crosslinking solution may be in the range from 1% to 50% by weight, such as in the range from 1.5% to 20% by weight, for example in the range from 2% to 5% by weight, based on the weight of the post-crosslinking solution.

The total amount of post-crosslinking solution may typically be in the range from 0.3% to 15% by weight, for example in the range from 2% to 6% by weight based on the base polymer. Examples of post cross linking may also be found in DE-A-12 239 074 or in German patent application 102004051242.6.

The superabsorbent polymer particles may have a particle size in the range from 45 μm to 4000 μm. Particle sizes used may range for example from 45 μm to 1000 μm, such as from 45-850 μm, for example from 100 μm to 850 μm.

Also, superabsorbent polymer particles having a narrow particle size distribution. Narrow particle size distributions are those in which not less than 80% by weight of the particles, for example not less than 90% by weight of the particles, for example not less than 95% by weight of the particles are within the selected range; this fraction can be determined using the sieve method of EDANA 420.2-02 "Particle Size Distribution". In some embodiments, the narrow particle size distributions may have a span of not more than 700 μm, or not more than 600 μm, for example less than 400 μm. Span here refers to the difference between the coarse sieve and the fine sieve which bound the distribution. In exemplary embodiments, particle size ranges used herein may for example be the fractions of 150-600 μm (span: 450 μm), of 200-700 μm (span: 500 μm), of 150-500 μm (span: 350 μm), of 150-300 μm (span: 150 μm), of 300-700 μm (span: 400 μm), of 400-800 μm (span: 400 μm), of 100-800 μm (span: 700 μm).

Block Popolymers

The block-copolymer comprised in the coating composition comprises at least four blocks being at least one soft block (A), sandwiched between at least two hard blocks (B) and at least one hydrophilic block (C).

Generally, block copolymers of such a structure may be obtained by any suitable method known to those skilled in the art. For example block copolymers may be obtained by sequential polymerization of chemically different monomers or by bonding preformed polymeric blocks to each other via suitable chemical reactions.

For example, the block copolymers described herein may be obtained by
  preparing a sequence of soft blocks(s) (A) and hard blocks (B), the sequence comprising at least three blocks being at least a first soft block, a first hard block and a second hard block wherein the first soft block is sandwiched between the first and second hard blocks (B),
  adding a hydrophilic block (C) to the sequence of soft and hard blocks.

The block copolymers may be prepared by living anionic polymerization.

B-A-B-C block copolymers may for example be obtained by the following steps:
  a) living anionic polymerization of first hard block B, wherein first hard block B has a living end;
  b) to the living end of first hard block B, soft block A is polymerized to give B-A, wherein A has a living end;

c) to the living end of soft block A, second hard block B is polymerized to give the sequence B-A-B, wherein second hard block has a living end; optionally repeating step b) and/or c) in any order to obtain for example a sequence B-(A-B)$_n$- wherein n is an integer being larger than 1.

d) to the living end of second hard block B, or optionally to the living end of the last block in embodiments wherein steps b) and/or c) have been repeated, the hydrophilic block is added;

and optionally further repeating step b,), c) and/or d) in any order

Addition of the hydrophilic block may be accomplished by polymerizing an additional block to the living chain end, which is either hydrophilic or subsequently rendered hydrophilic by suitable chemical reactions.

Generally, the sequence of soft block(s) and hard blocks may have at least two glass transition temperatures $Tg_1$ and $Tg_2$, respectively. Herein, glass transition temperatures $Tg_1$ and $Tg_2$ may for example be measured on a sample of the sequence of soft block(s) (and hard blocks before the hydrophilic block is added).

$Tg_1$ will typically be a lower temperature than $Tg_2$. For example, $Tg_1$ is below or equal to 20° C. and/or $Tg_2$ is above or equal to 40° C. $Tg_1$ and $Tg_2$ typically differ by at least 20° C.

After the addition of the hydrophilic block the Tg's of the block copolymer may be measured again. In such instances, an additional $Tg_{Hydrophil}$, which has not been detected for the sequence of soft and hard blocks, may be detected.

In certain embodiments, $Tg_{Hydrophil}$ may vary when water is added to the block copolymer. Typically, $Tg_{Hydrophil}$ decreases when water is added.

In embodiments wherein the sequence of soft and hard blocks has more than two different glass transition temperatures, $Tg_1$ refers to the glass transition temperature of the soft block having the highest Tg among all soft blocks, i.e. among all blocks having a glass transition temperature of less than 20° C., and $Tg_2$ refers to the glass transition temperature of the hard block having the lowest Tg of all hard blocks, i.e. among all blocks having a glass transition temperature of above 40° C.

In some embodiments, the block-copolymer may be a tetra-block-copolymer, i.e. comprises only four blocks of the general sequence (hard block)-(soft block)-(hard block)-(hydrophilic block), i.e. B-A-B-C.

The block copolymer may also be a multi-block-copolymer of the general structure -(B-A-B-C)$_n$-, wherein n is an integer typically having a value between 2 and 10. Such a multi-block copolymers may be obtained by preparing block copolymers of the structure B-A-B-C and linking them to each other by suitable chemical reactions known to the person skilled in the art in order to obtain -(B-A-B-C)$_n$-.

Also, in some embodiments multi-block-copolymers, the sequence of soft blocks and hard blocks may comprise more than one soft and two hard blocks. In such embodiments, the sequence of soft and hard blocks may be alternating, for example -A-B-A-B-A-B-.

Further, in some embodiments the block copolymer may comprise two hydrophilic blocks attached to each end of the sequence of soft block(s) and hard blocks, such as C-B-(A-B)$_n$-C, wherein n is an integer larger than or equal to 1, for example n may be in a range from 1 up to 10, or 2 up to 5. Typically, the hydrophilic block is not attached to a soft block.

While the different hard blocks may be composed of different monomeric units, it may be advantageous in order to simplify the synthesis that the hard blocks are composed of the same monomeric units. This may also apply to embodiments having more than one soft block. Thus, in certain embodiments, the block-copolymer may be a terpolymer, i.e. it comprises soft, hard and hydrophilic blocks, wherein all soft blocks are composed of the same soft monomeric units, all hard are composed of the same hard monomeric units and all hydrophilic blocks are composed of the same hydrophilic monomeric units.

To provide good transport of water based fluids through the coating into the superabsorbent polymer particles, the block copolymer may typically exhibit a WVTR (Water Vapor Transmission Rate) of at least 600 g/m$^2$/day, or at least 1000 g/m$^2$/day, or at least 3000 g/m$^2$/day, or at least 5000 g/m$^2$/day, or even at least 6000 g/m$^2$/day, when processed into a film and measured according to the WVTR method described herein. In some embodiments, the WVTR may generally be below 20000 g/m$^2$/day.

In order to accommodate swelling of the superabsorbent polymer particles, the block copolymer may exhibit a wet-elongation at break value of at least 300%, or at least 400% for example at least 1000% when processed into a film and measured according to the method herein. In some embodiments, the wet elongation at break may not be greater than 10000%. Also, it may be desirable for its application on superabsorbent particles, that the coating exhibits such extensibility in dry and in wet state.

To ensure good transport and interaction with water based liquids, the block copolymer may have a contact angle of less than 90°, or <70°, or <50°, or for example <40° when processed into a film according to the method herein.

Soft Block(s), Hard Blocks and Hydrophilic Block(s)

A block is typically composed of the same or similar monomeric units. Wherein same monomeric unit refers to monomeric units having the same chemical structure and similar refers to monomeric units selected from a given group, such as a group consisting of soft monomeric units, a group consisting of hard monomeric units or a group consisting of hydrophilic monomeric units i) Soft Block(s) (A)

A soft block typically comprises monomeric units which in the form of a polymeric block will give a soft block. Thus, such monomeric units are herein referred to as "soft monomeric units" and may be selected from the group consisting of butadiene, isoprene, $C_2$-$C_{30}$-alkyl-substituted 1,3-dienes, $C_1$-$C_{30}$-alkyl acrylates; hydrogenated versions of butadiene, hydrogenated versions of isoprene, hydrogenated versions of $C_2$-$C_{30}$-alkyl-substituted 1,3-dienes and combinations thereof.

In some embodiments, the soft monomeric units may be selected from the group consisting of butadiene, isoprene, $C_2$-$C_{30}$-alkyl-substituted 1,3-dienes, $C_4$-$C_{10}$-alkyl acrylates; hydrogenated versions of butadiene, hydrogenated versions of isoprene, hydrogenated versions of $C_2$-$C_{30}$-alkyl-substituted 1,3-dienes and combinations thereof.

For example, the soft monomeric units may be isoprene or butadiene.

Generally, the soft block may not be hydrophilic. For example, typically, the soft block may not comprise the hydrophilic monomeric units listed below.

The at least one soft block has a number average molecular weight of 20 000-200 000 g/mol, for example 30 000-60 000 g/mol.

Typically, a soft block has a glass transition temperature of less than 20° C., or less than 15° C., or less than 10° C., for example less than 0° C.

ii) Hard Block (B)

The at least two hard blocks typically comprise monomeric units which in the form of a polymeric block will give a hard block. Thus, such monomeric units are herein referred to as "hard monomeric units" and may be selected from the group consisting of styrene, $C_1$-$C_{30}$-alkyl-substituted styrenes, $C_1$-$C_{30}$-alkyl methacrylates, $C_1$-$C_3$-alkyl methacrylamides and combinations thereof.

In some embodiments, the hard nonnumeric units may be selected from the group consisting of styrene, $C_1$-$C_{30}$-alkyl-substituted styrenes, $C_1$-$C_4$-alkyl methacrylates, $C_1$-$C_3$-alkyl methacrylamides and combinations thereof.

Generally, the hard block may not be hydrophilic. For example, typically, the hard block may not comprise the hydrophilic monomeric units listed below.

Each of the at least two hard blocks have a number average molecular weight of 4 000-20 000 g/mol, for example 8 000-15 000 g/mol.

Typically, the hard block has a glass transition temperature of more than 40° C., or more than 50° C., or more than $6\beta°$ C.

iii) Hydrophilic Block (C)

The hydrophilic block can be obtained by polymerizing hydrophilic monomers, or by polymerizing monomers which can be rendered hydrophilic by means of chemical reaction in a subsequent step. Irrespective of the chemical procedure, "hydrophilic monomer unit" as used herein refers to the structure of the monomers in the final block copolymer. Thus, both, monomers which are hydrophilic before polymerization and monomers which have been treated hydrophilic by means of a chemical reaction after polymerization will be referred to as hydrophilic monomer units.

Thus, it may be appreciated that the hydrophilic block may be prepared by polymerizing monomers which not hydrophilic, but capable of being rendered hydrophilic by subsequent chemical reactions, into a "hydrophilic block precursor" and subsequently transforming the hydrophilic block precursor into the hydrophilic block (C).

Typical hydrophilic monomer units may be selected form the group consisting of acrylic acid and salts thereof, methacrylic acid and salts thereof, itaconic acid and salts thereof, dialkylaminoacrylates and quaternary salts thereof, dialkylaminomethacrylates and quaternary salts thereof, dialakylaminoacrylamides and quaternary salts thereof, dialakylaminomethacrylamides and quaternary salts thereof, quaternary salts of vinyl pyridine, ethyleneoxide and ethylene oxide-alkylene oxide copolymers, styrene sulfonic acid and salts thereof and ethylene oxide macromers of acrylates or methacrylates; and combinations thereof.

In some embodiments, the hydrophilic monomer units may be selected from the group consisting of acrylic and salts thereof; methacrylic acid and salts thereof, dialkylaminomethacrylates, dialkylaminomethacrylamides, ethyleneoxide and alkylene oxide copolymers, styrene sulfonic acid and salts thereof, and ethylene oxide macromers of acrylates or methacrylates.

The hydrophilic block may comprise 5-50%, or 15-30% by weight of the block copolymer. In embodiments comprising more than one hydrophilic block, the sum of all weights of the hydrophilic blocks comprise 5-50%, or 15-30% relative to the weight of the entire final block copolymer.

The hydrophilic block may have a number average of molecular weight in the range from 1400-240 000 g/mol. In some embodiments, the hydrophilic block may have a number average of molecular weight in the range from 4 200-72 000 g/mol.

The hydrophilic block (C), may comprise at least 10 hydrophilic monomer units directly bound to each other.

Coated Superabsorbent Particles

The block copolymer may be coated onto the superabsorbent polymer particles by applying it in any form, for example in the form of a melt, such as a hot melt, or in form of the coating composition described herein.

The coated superabsorbent particles may comprise from 0.01% to 15%, or from 0.1% to 5% for example from 0.5% to 2% of block copolymer relative to the weight of the (uncoated) superabsorbent particles.

For example, the block copolymer may be applied from a solution. The solution may be prepared such that the block copolymer is present in the solution in an amount form 0.5-2% relative to the weight of the uncoated superabsorbent polymer particles which are also added to the solution.

Coating Composition

The block copolymer herein may be applied to the super absorbent polymer particles per se, or in the form of a coating composition. When applied to the superabsorbent polymer particles as a coating composition, it may comprise a carrier and the block copolymer described below. The carrier may typically be a solvent, such as THF (tetrahydrofuran), toluene, di-n-hexyl phthalate, ethyl acetate, diamyl phthalate, dibutyl sebacate, benzene, chloroform, dibutyl phthalate or methyl ethyl ketone.

Generally, the carrier may be present in any suitable amount such as from 1% to 99%, or from about 30% to about 95%, relative to the weight of the coating composition.

In some embodiments, the carrier may only be present in low amounts, such as 1-10%, or 2-5% relative to the weight of the coating composition.

In some embodiments, the coating composition typically comprises at least 85 wt %, or 90 wt %, for example 95 wt % of the block copolymer described below relative to the weight of the coating composition. In some embodiments, the coating composition consists of the block copolymer.

In some embodiments, higher amounts of carrier may be desirable, such as from 10% to 99%, or from 30% to 95%, relative to the weight of the coating composition.

Optionally, the coating composition may further comprise small amounts of other ingredients, such as antioxidants, UV-stabilizers, organic or inorganic fillers and/or surfactants. Small amount herein typically refers to amounts of less than 2 wt %, or less than 1 wt %, for example less than 0.1 wt % relative to the weight of the coating composition.

Typically, when the block copolymer is applied to the superabsorbent particles in form of the described coating composition to form the coated superabsorbent polymer particles, the carrier may not be present in the coating which has been formed. Typically the carrier is evaporated from the coating. However, small amounts may remain present such as less than 5%, or less than 3%, or for example less than 1% by weight of the block copolymer.

Process for Making the Coated Superabsorbent Particles

The process comprises the steps of:
a) obtaining superabsorbent polymer particles;
b) simultaneously with or subsequently to step a), applying the block copolymer or the coating composition comprising the block copolymer to at least a part of said superabsorbent polymer particles; and optionally the step of
c) annealing the resulting coated superabsorbent polymer particles of step b),
to obtain the coated superabsorbent polymer particles herein.

In step a) 'obtaining' the superabsorbent polymer particles, as described herein above, includes using commercially available superabsorbent polymer particles, or forming the superabsorbent polymer particles by any known process.

The coating step b) may be done by any known method, for example by mixing or dispersing the superabsorbent polymer particles in the coating composition or in a melt comprising the block copolymer; by spraying the coating composition, or the melt onto the superabsorbent polymer particles; by introducing the coating composition, or the melt and the superabsorbent polymers in a fluidised bed or Wurster coater; by agglomerating the coating composition, or the melt and the superabsorbent polymers; by dip-coating the superabsorbent polymers particles in the coating composition, or the melt. Other suitable mixers include for example twin drum mixers, so called "Zig-Zag" mixers, plough-share mixers, such as Lödige mixers, cone screw mixers, or perpendicularly cylindrical mixers having coaxially rotating blades. Further examples of coating processes are described in U.S. Pat. No. 5,840,329 and U.S. Pat. No. 6,387,495.

In an alternative embodiment of the invention, the coating step b) may be done by applying the coating composition in the form of a foam, for example an open-cell foam, leading to a porous coating. In yet an alternative embodiment the coating step may be done by forming a fibrous network on the surface of the superabsorbent material such as for example by applying the coating composition in the form of meltblown microfibers, such that an essentially connected coating is formed.

For its application to the superabsorbent polymer particles, the coating composition may comprise solvents, such as THF (tetrahydrofuran), toluene, di-n-hexyl phthalate, ethyl acetate, diamyl phthalate, dibutyl sebacate, benzene, chloroform, dibutyl phthalate or methyl ethyl ketone.

In embodiments where the coating composition is provided in the form of a solution or a dispersion, processing aids may be added subsequently or prior to the coating step b), e.g. in order to aid a good film formation of the coating.

In the optional step c), the resulting coated superabsorbent polymer particles may be annealed. The optional annealing step c) typically leads to a further strengthened or more continuous or more completely connected coating and it may eliminate defects.

Typically, the annealing step) involves a heat treatment of the coated superabsorbent polymer particles; it may be done by for example radiation heating, oven heating, convection heating, azeotropic heating, and it may for example take place in conventional equipment used for drying, such as fluidized bed driers. In some embodiments, a vacuum may be applied as well. In alternative embodiments, the annealing may be done under an inert gas (to avoid oxidation).

The annealing step typically involves heating the coated superabsorbent polymer particles at a temperature which is above the highest Tg of the block copolymer, such as to a temperature which is at least 20° C. above said highest Tg, for example at least 50° C. above the highest Tg.

On the other hand, if the superabsorbent polymer particles have a melting temperature Tm, then the annealing step should be conducted at least 20° C. below the Tm and if possible and at least 20° C., for example at least 50° C. above the highest Tg.

Generally, the superabsorbent polymer particles shall not be heated to a temperature above their decomposition temperature.

The annealing step may be done for, for example, at least 5 minutes, or for at least 10 minutes or for at least 15 minutes, or at least 30 minutes or at least 1 hour for example at least 2 hours.

This annealing step may be done once, or it may be repeated, for example the annealing step may be repeated with different temperatures, for example first at a lower temperature, and subsequently at a higher temperature.

Typically, the temperature and time are adjusted in order to allow good coating (film) formation, such as to increase the mechanical stability of the coatings (films).

During the annealing step, the coated superabsorbent polymer particles may also be dried at the same time. Alternatively or in addition, a separate drying step may be conducted.

The final coated superabsorbent particles are typically solid and thus, in some embodiments a subsequent process step may be conducted to solidify or further solidify the resulting coated superabsorbent polymer particle of step b), also known in the art as solidifying or particle forming step. This may for example be done prior to, or simultaneously with step c).

Subsequently, known particle forming processes may be used including agglomeration, extrusion, grinding and optionally followed by sieving in order to modify the particle size distribution.

The process may also involve addition of further processing aids in any of the steps, such as granulation aids, flow aids, drying aids. Any flow aids known in the art may be added (for example prior to or during the coating step, or for example during the drying and/or annealing step, as discussed below; for example Aerosil 200, available from Degussa has been found to be a good flow aid).

For example, the process may involve addition of a spreading aid and/or surfactant which facilitates the coating step b).

Absorbent Articles

The coated superabsorbent polymer particles of the invention are useful in a number of applications, including in absorbent structures such as disposable absorbent articles, such as interlabial products, sanitary napkins, panty liners, and adult incontinent products, baby diapers, nappies and training pants. The coated superabsorbent polymer particles described herein may be used in acquisition systems of such absorbent articles, or for example, in absorbent cores thereof.

FIG. 1 is a plan view of a diaper 20 as an embodiment of an absorbent article. The diaper is shown in its flat out, uncontracted state (i.e., without elastic induced contraction). Portions of the structure are cut away to more clearly show the underlying structure of the diaper 20. The portion of the diaper 20 that contacts a wearer is facing the viewer.

The diaper 20 has a length along a longitudinal axis 100 and a width along a transverse axis 110. The periphery of the diaper 20 is defined by the outer edges of the diaper 20 in which the longitudinal edges 44 run generally parallel to the longitudinal axis 100 of the diaper 20 and the end edges 46 run generally parallel to the transverse axis 110 of the diaper 20.

The chassis 22 of the diaper 20 in FIG. 1 comprises the main body of the diaper 20. The chassis 22 comprises an outer covering including a liquid pervious topsheet 24 and/or a liquid impervious backsheet 26. The entire absorbent core 28 is encased between the topsheet 24 and the backsheet 26.

Optionally, the diaper 20 comprises an acquisition system to acquire and temporarily store fluids discharged from the body. Such an acquisition system may be deposited between the absorbent core 28 and the topsheet 24.

The chassis 22 may further include side panels 30, leg cuffs 32 with elastic members 33 and a waist feature 34. The leg cuffs 32 and the waist feature 34 typically comprise elastic members.

One end portion of the diaper is configured as the front waist region 36 of the diaper 20. The opposite end portion is configured as the rear waist region 38 of the diaper 20. The intermediate portion of the diaper is configured as the crotch region 37, which extends longitudinally between the front and rear waist regions. The crotch region 37 is that portion of the diaper 20 which, when the diaper is worn, is generally positioned between the wearer's legs.

The waist regions 36 and 38 may include a fastening system comprising fastening members 40 may be attached to the rear waist region 38 and a landing zone 42 attached to the front waist region 36. Alternatively, the rear waist region may be permanently bonded to the front waist region to from a pant-type diaper having a waist opening and two leg openings.

In one embodiment the topsheet of the absorbent garment can be apertured, i.e. the topsheet has a plurality of apertures having an aperture size of at least about $0.2$ $mm^2$. The topsheet may have an open area of at least about 10%, the open area being the sum of all apertures. The method to determine the aperture size and open area of the apertured topsheet is disclosed in EP 0953324.

The diaper may also include other features as are known in the art including front and rear ear panels, elastics and the like to provide better fit, containment and aesthetic characteristics.

Absorbent Core

An absorbent core has two major sides, a first side facing the body of the wearer when the absorbent article is worn and a second side facing the garment when the absorbent article is worn. Accordingly, the first and second side may also be referred to as body-facing and garment facing side.

The absorbent core has a length along an x-axis, a width, smaller than the length, along a y-axis and a height, smaller than the width, along a z-axis.

In certain embodiments, the absorbent core may be of rectangular shape. In other embodiments the core may have curved edges. For example, the core may be of an hourglass shape.

The absorbent core may comprise a core wrap, the coated superabsorbent particles described herein and, optionally other absorbent materials which are known to those skilled in the art. Optionally, the absorbent core comprises one or more glues, surfactants, binders, colors, pigments, perfume, lotion(s), opacity enhancers, nonwovens, odor control materials or materials to increase the dry/wet integrity of the core, such as structural elements.

The core wrap is used to cover the absorbent material. In certain embodiments the absorbent material and, if present, the core glue may either be sandwiched between two separately provided sheets of core wrap material, or may be wrapped by folding one sheet of core wrap material, for example in a C-fold, to envelope the absorbent material and, optionally, the core glue.

In one embodiment the absorbent core may for example comprise as a core wrap a nonwoven fabric. The absorbent material, such as the superabsorbent polymer material may then be deposited on the nonwoven fabric. If present, the core glue may be deposited such that it at least partly covers or enlaces the absorbent material on the nonwoven fabric.

The amounts of materials used in the absorbent core herein are given in % by weight relative to the basis weight of the whole absorbent core including the core wrap. The basis weight of the absorbent core is given in $g/cm^2$. The basis weight may be determined by weighing the whole absorbent core. The obtained weight is then divided by the area enclosed by the perimeter line.

The absorbent core may comprise a relatively high amount of superabsorbent polymer material of more than 80%, 85%, 90%, or 95% by weight of the absorbent core.

In certain embodiments, the absorbent core comprises less than 20%, or 15% or 10% or 5% by weight of the absorbent core of airfelt material.

In one embodiment, the absorbent core may be substantially free of, or completely free of airfelt material wherein "substantially free of" means that less than 1% by weight of the absorbent core comprises airfelt material and "completely free of" means that 0% by weight of the absorbent core consist of airfelt material.

According to certain embodiments, the absorbent core consists essentially of superabsorbent polymer material, core glue and a core wrap. In such an embodiment the amounts of these materials may add up to present up to 99%, for example 100% by weight of the absorbent core.

EXAMPLES

Monomer Purification

Monomers are purified to a grade suitable for conducting living anionic polymerization reactions. Means of purification, as for example described with regard to isoprene or styrene in the context of example 1, are known to those skilled in the art.

Example 1

Synthesis of Block-copolymer poly(styrene-b-isoprene-b-styrene) Precursor

Styrene Purification

Styrene (Aldrich) is purified by passing through an activated alumina (available from Aldrich) column under nitrogen atmosphere to remove inhibitors and then the styrene is added to a clean, dry round bottom flask filled with nitrogen and fitted with rubber septa.

Isoprene Purification

Isoprene (Aldrich) is purified by passing through an activated alumina column under nitrogen atmosphere to remove inhibitors and then the isoprene is added to a clean, dry round bottom flask filled with nitrogen and fitted with rubber septa.

To a clean reactor at 60° C., are added 3 liters of cyclohexane (pesticide residue analysis (PRA) grade from Aldrich) and 60 g of styrene (Aldrich). This is titrated with s-butyl lithium to a persistent yellow color and 5 mmole of butyl lithium is added to give the desired molecular weight. After 20 minutes a sample is taken and 280 grams of isoprene (Aldrich) is added to the reactor. This is allowed to react for 45 minutes maintaining the temperature at 60° C. A sample is taken for analysis and 60 grams of styrene is added. After 20 minutes a 20 gram sample is taken for analysis and testing. The living polymer anion is then ready for further reaction in subsequent examples.

The molecular weight of the first block is found to be 12,800 g/mole. The triblock is found to have a molecular weight of 80,000 g/mole with a composition of 27 weight percent styrene, 73 weight percent isoprene.

Example 2

Synthesis of poly(styrene-b-isoprene-b-styrene-t-tert-butylmethacrylate)

500 ml of the reaction product from Example 1 is diluted in 1500 ml of THF containing 2.5 mmole of 1,1-diphenylethylene (Aldrich) and then cooled to −78° C. To this solution is added 37.5 grams of purified t-butyl methacrylate (TCI America). After 20 minutes, 1 ml of methanol is added. The reaction is warmed to room temperature and the polymer is isolated by precipitation from methanol. The polymer is stabilized by addition of 0.2 g of Irganox 1010 (Ciba). The polymer is found to have a molecular weight of 100K g/mole with a composition of 30 weight percent (poly)t-butyl-methacrylate.

Example 3

Synthesis of poly(styrene-b-isoprene-b-styrene-b-glycidylmethacrylate)

500 ml of the reaction product from Example 1 is diluted in 1500 ml THF containing 2.5 mmole of 1,1-diphenylethylene (Aldrich) and then cooled to −78° C. To this solution is added 5 grams of purified glycidyl methacrylate (Aldrich).

Example 4

Synthesis of poly(styrene-b-isoprene-b-methacrylic Acid 25 grams of the poly(styrene-b-isoprene-b-styrene-b-tert-butylmethacrylate) material from Example 2 is dissolved in 500 ml of toluene (Aldrich) and to this added 0.2 grams of p-toluene-sulfonic acid (Aldrich) along with 0.5 grams of Irganox 1010 (Ciba). The reaction is heated to reflux and isobutylene gas is evolved over a period of minutes. After 45 minutes of reflux, the solution is cooled and the product is isolated by precipitation from methanol (Aldrich). 0.1 g of Irganox 1010 (Ciba) is added to the polymer which is then vacuum dried.

Example 5

Synthesis of poly(styrene-b-isoprene-b-styrene-b-methacryoxy-polyethylene oxide (1K))

500 ml of the poly(styrene-b-isoprene-b-styrene-b-glycidylmethacrylate) material from Example 3 is reacted with 50 grams of Jeffamine M1000 polymer from Huntsman Chemical. The product obtained is poly(styrene-b-isoprene-b-styrene-b-methacryoxy-polyethylene oxide).

Example 6

Synthesis of poly(styrene-b-isoprene-b-styrene-b-methacryoxy-polyethylene oxide (2K))

500 ml of the poly(styrene-b-isoprene-b-styrene-b-glycidylmethacrylate) material from Example 3 is reacted with 50 grams of Jeffamine M-2070 polymer from Huntsman Chemical. The product obtained is poly(styrene-b-isoprene-b-styrene-b-methacryoxy-polyethylene oxide).

Example 7

Synthesis of poly(styrene-b-t-butylstyrene-b-1,2-butadiene-b-tbutylstyrene)

To a clean reactor at 25 C, are added 3 liters of cyclohexane (PRA grade from Aldrich) and 3.6 grams of Tetrahydrofuran (Aldrich) and 62 grams of styrene (Aldrich). This is titrated with s-butyl lithium to a persistent yellow color and 3.1 mmole of s-butyl lithium is added to give the desired molecular weight. After 20 minutes a sample is taken and 27 grams of t-butyl styrene (Aldrich) and this is allowed to react for 30 minutes. After 30 minutes a sample is taken and 112 grams of butadiene (Electronics grade Matheson Gas) is added to the reactor. This is allowed to react for 240 minutes maintaining the temperature at 25° C. A sample is taken for analysis and 27 grams of t-butyl styrene is added. After 20 minutes the reaction is terminated by addition of methanol. The reaction solution is stabilized with 0.25 grams of Irganox 1010 and vacuum dried.

Example 8

Preparation of Nickel Hydrogenation Catalyst

Hydrogenation catalyst is prepared as follows; 0.345 g of nickel(2-ethyl hexanoate) (Aldrich) is dissolved in 30 ml of cylcohexane (PRA grade VWR). To this is added 3 ml of triethylaluminum (Aldrich) (1.0M in hexanes) resulting in a black dispersion of nickel catalyst.

Example 9

Synthesis of poly(styrene-t-butylstyrene-b-ethylene-butene-b-t-butylstyrene)

100 grams of the poly(styrene-b-t-butylstyrene-b-1,2-butadiene-b-t-butylstyrene) from Example 7 is dissolved in 2000 ml of cyclohexane and the butadiene block is hydrogenated with a Nickel catalyst as prepared in example 8. The catalyst is added via syringe to the polymer solution and hydrogen gas is added to the reaction at 50 psi with stirring until substantially complete hydrogenation of the butadiene block occurs. Samples are taken for analysis to confirm hydrogenation of the butadiene block and an additional batch of catalyst is required to complete the hydrogenation.

Example 10

Preparation of Acetyl Sulfate

A solution of acetyl sulfate is prepared as follows. To 100 ml of methylene chloride (Aldrich) is added 200 ml of acetic anhydride (Aldrich) and this is cooled to 0° C. To this is slowly added 55.5 ml of sulfuric acid (Aldrich). This is allowed to react for 60 minutes at 0° C.

Example 11

Synthesis of poly(styrenesulfonate-b-t-butylstyrene-b-ethylene-butene-b-t-butylstyrene)

20 grams of the poly(styrene-b-t-butylstyrene-b-ethylene-butene-b-t-butylstyrene) from example 9 is dissolved in methylene chloride (Aldrich) at 0° C., to which is added 100 ml of the acetyl sulfate prepared in Example 10. This is reacted for 120 minutes to prepare the poly(styrenesulfonate-b-t-butylstyrene-b-ethylene-butene-b-t-butylstyrene).

Example 12

Synthesis of poly(styrene-b-isoprene-b-styrene-b-methacrylic Acid diethanolamine Salt 10 grams of the polymer from Example 4 is dissolved in 100 ml of THF (Aldrich) and neutralized with 1.3 grams of diethanolamine. The solution is cast into a Teflon dish to form a film with a diameter of 4 inches.

Example 13

10 grams of the polymer from Example 5 is dissolved in 100 ml of THF (Aldrich). 12 mL of the solution is cast into a flat bottomed 4 inch Teflon dish to form a film. The solvent (typically THF) is allowed to evaporate at 25° C. and 40-60% humidity overnight and subsequently vacuum dried at 40° C. for 16 hours. After that, the film is peeled from the dish. Suitable sample sizes are cut from the film. DSC analysis of the polymer indicates glass transition temperatures at −61 C and at +65 C.

Example 14

10 grams of the polymer from Example 6 is dissolved in 100 ml of THF (Aldrich). 12 mL of the solution is cast into a flat bottomed 4 inch Teflon dish to form a film. The solvent (typically THF) is allowed to evaporate at 25° C. and 40-60% humidity overnight and subsequently vacuum dried at 40° C. for 16 hours. After that, the film is peeled from the dish. Suitable sample sizes are cut from the film. DSC analysis of the polymer indicates glass transition temperatures at −61 C and at +64 C.

Example 15

10 grams of the polymer from Example 11 is dissolved in 100 ml of THF (Aldrich). 12 mL of the solution is cast into a flat bottomed 4 inch Teflon dish to form a film. The solvent (typically THF) is allowed to evaporate at 25° C. and 40-60% humidity overnight and subsequently vacuum dried at 40° C. for 16 hours. After that, the film is peeled from the dish. Suitable sample sizes are cut from the film. DSC analysis of the polymer indicates glass transition temperatures at −53 C and at +57 C.

Example 16

10 grams of the polymer from Example 1 is dissolved in 100 ml of THF (Aldrich). 12 mL of the solution is cast into a flat bottomed 4 inch Teflon dish to form a film. The solvent (typically THF) is allowed to evaporate at 25° C. and 40-60% humidity overnight and subsequently vacuum dried at 40° C. for 16 hours. After that, the film is peeled from the dish. Suitable sample sizes are cut from the film. DSC analysis of the polymer indicates glass transition temperatures at −61 C and at +65 C.

Examples 17-21

Films as prepared in examples 12-16 are cut to circles with a diameter of 2⅞ inches which are then mounted into MVTR cups from Gardco (Paul N Gardner Co.) containing deionized water. These cups/water/films are placed on 4 digit balances contained within a dry box and the weight with time measurements are taken for 8 hours. Humidity is kept low by sweeping the box with dry nitrogen gas. The WVTR values are determined from the average rate of three films measured as described.

TABLE 1

WVTR values and contact angles of films prepared form the block copolymer examples

| Sample | Film | Thickness in mm | WVTR in grams/m²/day | Contact Angle |
| --- | --- | --- | --- | --- |
| Example 17 | Example 12 | 0.15 | 6000 | 38° |
| Example 18 | Example 13 | 0.15 | 1100 | 64° |
| Example 19 | Example 14 | 0.15 | 900 | 78° |
| Example 20 | Example 15 | 0.15 | 2500 | |
| Example 21 | Example 16 | 0.15 | 200 | 104° |

TABLE 2

Wet elongation at break values of films prepared form the block copolymer examples

| Sample | Peak Load in N | Peak Strain in % |
| --- | --- | --- |
| Example 18 | 5.99 | 1141.66 |
| Example 19 | 8.81 | 1991.11 |
| Example 17 | 14.81 | 302.22 |

TABLE 3 structural formulas of block copolymers

| Sample | Blockcopolymer | Chemical formula of block copolymer |
| --- | --- | --- |
| Example 17 | Example 4 | [structure: block copolymer with styrene ($n$), isoprene ($m$), styrene ($n$), and methacrylate blocks ($p$, $p-x$) bearing −C(=O)OH and −C(=O)O⁻ $^+$NHR$_3$ groups] |

TABLE 3-continued structural formulas of block copolymers

| Sample | Blockcopolymer | Chemical formula of block copolymer |
|---|---|---|
| Example 18 | Example 5 | *(structure: styrene–isoprene–styrene–acrylate block with pendant –C(=O)–O–CH$_2$–CH(OH)–CH$_2$–NH–PEO)* |
| Example 19 | Example 6 | *(structure: styrene–isoprene–styrene–acrylate block with pendant –C(=O)–O–CH$_2$–CH(OH)–CH$_2$–NH–PEO)* |
| Example 20 | Example 11 | *(structure: poly(styrene sulfonic acid)–poly(t-butylstyrene)–polyolefin–poly(t-butylstyrene) block copolymer with SO$_3$H and C(CH$_3$)$_3$ substituents)* |
| Example 21 | Example 1 | *(structure: styrene–isoprene–styrene triblock copolymer)* |

Methods of Measurement

Film Formation

The polymer films used for the methods herein are prepared by solution casting the film into a flat bottomed 4 inch Teflon® dish using 12 mL of a solution comprising 10 g of the block copolymer dissolved in 100 mL of a solvent. The solvent (typically THF) is allowed to evaporate at 25° C. and 40-60% humidity overnight and subsequently vacuum dried at 40° C. for 16 hours. After that, the film is peeled from the dish. Suitable sample sizes are cut from the film.

Water Vapor Transmission Rate (WVTR)

Using the ASTM method E 96-80 as a guide, the water vapor transmission of polymers is tested via the water method using Gardco cups. These cups have an opening of 5.64 cm in diameter, which corresponds to an open surface area of 25 square cm.

The films are cut to a diameter of $2_{7/8}$ inches with a film punch.

Two 3 mm holes are punched into the film on opposite sides for mounting the film over the pins of the cup to secure the film in position.

The cup is partially filled with water leaving an air space of at least ¼ inch above the water level. The cup is coated with a silicone grease around the edge and the film is pushed down into the silicone and the top of the cup is tightened down onto the edges of the polymer film.

Sample cups are placed onto a balance having an accuracy of +/−0.0001 g in an environmental enclosure with continuous nitrogen purge to maintain low humidity. The enclosure humidity is monitored with time to confirm the relative humidity is below 10%.

The weights of the samples are taken at one minute intervals for 16 hours with the WVTR value determined over the first 4 hours of the experiment.

The data is plotted weight change versus time in hours, and the slope is taken with units of grams/25 sq cm/hour. Translation of this to grams/sq meter/day involves multiplying the slope of the data by 9600. The value 9600 comes from the factor of 24 hours per day and a factor of 40 to convert the 25 sq cm opening to square meters.

Contact Angle Measurement

The contact angle measurements where conducted using the ASTM method D5946-09 as a guide. All testing has been conducted at a temperature of 25° C. and a relative humidity of 60-70°. The following adaptations have been made:
7. Apparatus: 7.1 Contact Angle Meter, or Goniometer—The experiments have been conducted on a FTA 200 from First Ten Angstroms, Inc.
8. Reagents and Materials: 8.1 Purity of Water—Millipore water has been used for the testing purposes.
9. Sampling: 9.1 Films of the size of 1 cm×1 cm have been used for the contact angle measurement.
10. Conditioning: 10.1 No special conditioning has been performed on the films.
11. Procedure: 11.2 Suspend a 5 to 8-μL droplet at the end of a blunt ended 22 gauge syringe needle from a 10 ml syringe. 11.3 Within 5 sec of the drop transferring to the film an image is taken. The image is then analyzed by the First Ten Angstrom software package. 11.4 Advance the sample to place the next droplet onto a previously untouched area. 11.5 Take three contact angle measurements on the sample.
12. Calculation: 12.1.1 Calculate the average of the three measurements.

Wet-Elongation at Break Test

This test method is used to measure the wet-elongation at break (=extensibility at break). A preferred piece of equipment to do the tests is a tensile tester such as an Instron 5544, fitted with a computer interface and heated environmental chamber and Bluehill Software, available from Instron Corporation with a 100N load cell. This measures the Constant Rate of Extension in which the pulling grip moves at a uniform rate. The load cell is selected such that the measured load (e.g., force) of the tested samples is between 10 and 90% of the capacity of the load cell.

Each sample is die-cut from a film, each being 2"×0.5" using a die cutter with a clicker press to cut the film into individual samples A minimum of three samples are chosen which are substantially free of visible defects such as air bubbles, holes, inclusions, and cuts. They should also have smooth and substantially defect-free edges.

The samples are then swollen in 0.9% Saline overnight at 25° C. before being tested. The samples are then removed from the saline and the excess saline is allowed to drain off the sample before it is loaded into pneumatic line grips with a gage length of one inch that are attached to the precalibrated 100 N Load Cell on the Instron 5544 Testing System running the Bluehill software package with its environmental chamber set to 38° C. The sample is then strained at a rate of 254 mm/min (10 in/min) until it breaks. The force (N) and strain (%) at which it breaks is then recorded.

Glass Transition Temperatures

Glass Transition Temperatures (Tg's) are determined for the purpose of this invention by differential scanning calorimetry (DSC). The calorimeter should be capable of heating/cooling rates of at least 20° C./min over a temperature range, which includes the expected Tg's of the sample that is to be tested, e.g. of from −90° to 250° C., and the calorimeter should have a sensitivity of about 0.2 μW. TA Instruments Q1000 DSC is well-suited to determining the Tg's referred to herein. The material of interest can be analyzed using a temperature program such as: equilibrate at −90° C., ramp at 20° C./min to 120° C., hold isothermal for 5 minutes, ramp 20° C./min to −90° C., hold isothermal for 5 minutes, ramp 20° C./min to 250° C. The data (heat flow versus temperature) from the second heat cycle is used to calculate the Tg via a standard half extrapolated heat capacity temperature algorithm. Typically, 3-5 mg of a sample material is weighed (+/−0.1 g) into an aluminum DSC pan with crimped lid.

Herein, Tg1 and Tg2 can be measured on a sample of the sequence of hard and soft block(s) before the hydrophilic block is added.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. Coated superabsorbent polymer particles, being coated with a block copolymer, wherein the block copolymer is obtained by the process of:
   (i) preparing a sequence of soft block(s) (A) and hard blocks (B), the sequence comprising at least three blocks being at least a first soft block, a first hard block and a second hard block wherein the first soft block is sandwiched between the first and second hard blocks (B); and
   (ii) combining the sequence of soft block(s) and hard blocks with a hydrophilic block (C) block, or combining the sequence of soft block(s) and hard blocks with a hydrophilic block precursor and subsequently transforming the hydrophilic block precursor into the hydrophilic block (C).

2. The coated superabsorbent polymer particles of claim 1, wherein the hydrophilic block (C), comprises at least about 10 hydrophilic monomer units directly bound to each other.

3. The coated superabsorbent polymer particles of claim 1, wherein the hydrophilic block (C), comprises from about 5 to about 50%, by weight, of the block copolymer.

4. The coated superabsorbent polymer particles of claim 1, wherein the block copolymer is present in an amount of from about 0.5 to about 2%, by weight, relative to the weight of the coated superabsorbent polymer particles.

5. The coated superabsorbent polymer particles of claim 1, wherein the sequence of soft block(s) and hard blocks has at least two glass transition temperatures $Tg_1$ and $Tg_2$, wherein $Tg_1$ and $Tg_2$ differ by at least about 20° C.

6. The superabsorbent polymer particles according to claim 5, wherein $Tg_1 \leqq$ about 20° C., $Tg_2 \geqq$ about 40° C., or both.

7. The coated superabsorbent polymer particles of claim 1, wherein the hydrophilic block is comprised of hydrophilic monomeric units comprising one or more functional groups selected from the group consisting of: acid groups in their free acid or salt form, ether groups, amine functionalized groups, quaternary ammonium groups, alcoholic groups and combinations thereof.

8. The coated superabsorbent polymer particles of claim 1, wherein the superabsorbent polymers comprised by the superabsorbent particles are obtained by first forming a base polymer by polymerization of a monomer solution comprising:
  i) at least one ethylenically unsaturated acid-functional monomer, and
  ii) at least one crosslinker,
  wherein the superabsorbent polymer obtained thereby is dried.

9. The coated superabsorbent polymer particles of claim 1, wherein the at least one hydrophilic block comprises monomeric units selected from the group consisting of: acrylic acid and salts thereof, methacrylic acid and salts thereof, itaconic acid and salts thereof, dialkylaminoacrylates and quaternary salts thereof, dialkylaminomethacrylates and quaternary salts thereof, dialakylaminoacrylamides and quaternary salts thereof, dialkylaminomethacrylamides and quaternary salts thereof, quaternary salts of vinyl pyridine, ethyleneoxide and ethylene oxide-alkylene oxide copolymers, styrene sulfonic acid and salts thereof and ethylene oxide macromers of acrylates or methacrylates; and combinations thereof.

10. The coated superabsorbent polymer particles of claim 1, wherein the at least one soft block comprises monomeric units selected from the group consisting of butadiene, isoprene, $C_2$-$C_{30}$-alkyl-substituted 1,3-dienes, $C_1$-$C_{30}$-alkyl acrylates; hydrogenated versions of butadiene, hydrogenated versions of isoprene, hydrogenated versions of $C_2$-$C_{30}$-alkyl-substituted 1,3-dienes and combinations thereof; and
  wherein the at least two hard blocks comprise monomer units selected from the group consisting of: styrene, $C_1$-$C_{30}$-alkyl-substituted styrenes, $C_1$-$C_{30}$-alkyl methacrylates, $C_1$-$C_3$-alkyl methacrylamides, and combinations thereof.

11. The coated superabsorbent polymer particles of claim 1, wherein the block copolymer is a tetra-block copolymer wherein the four blocks are arranged in the sequence B-A-B-C.

12. The coated superabsorbent polymer particles of claim 1, wherein the first soft block has a number average molecular weight of about 20,000 to about 200,000 g/mol; and
  wherein each of the at least two hard blocks have a number average molecular weight of about 4,000 to about 20,000 g/mol.

13. The coated superabsorbent polymer particles of claim 1, wherein the block copolymer used for the coating exhibits a WVTR of at least about 600 g/m$^2$/day when processed into a film and measured according to the WVTR method described herein.

14. The coated superabsorbent polymer particles of claim 1, wherein the block copolymer used for the coating exhibits a wet-elongation at break value of at least about 300% when processed into a film and measured according to the method herein.

15. The coated superabsorbent polymer particles of claim 1, wherein the contact angle measured on a film prepared from the sequence of soft block(s) and hard blocks is higher than the contact angle of the block copolymer when prepared into a film according to the method given herein.

16. The coated superabsorbent polymer particles of claim 1, wherein the block copolymer used for the coating has a contact angle of less than about 90° when processed into a film according to the method herein.

17. The coated superabsorbent polymer particles of claim 1, having a particle size within the range of about 45 μm to about 4000 μm.

18. An absorbent article comprising the coated superabsorbent particles of claim 1.

19. The absorbent article of claim 18 further comprising an absorbent core, wherein the coated superabsorbent particles are comprised in the absorbent core.

20. A process for making the coated superabsorbent particles comprising the steps of:
  (i) providing superabsorbent particles;
  (ii) providing a block copolymer or a coating composition comprising the block copolymer;
  (iii) coating the superabsorbent particles with the block copolymer or the coating composition;
  wherein the block copolymer is obtained by the process of:
  (i) preparing a sequence of soft block(s) (A) and hard blocks (B), the sequence comprising at least three blocks being at least a first soft block, a first hard block and a second hard block wherein the first soft block is sandwiched between the first and second hard blocks (B),
  (ii) combining the sequence of soft block(s) and hard blocks with a hydrophilic block (C) block, or combining the sequence of soft block(s) and hard blocks with a hydrophilic block precursor and subsequently transforming the hydrophilic block precursor into the hydrophilic block (C).

21. The process of claim 20, further comprising the step(s) of drying and/or annealing the coated superabsorbent particles.

* * * * *